(12) United States Patent
Oh

(10) Patent No.: US 10,702,631 B2
(45) Date of Patent: Jul. 7, 2020

(54) CORE-CENTERED HYDROXYAPATITE GRANULE COMPOSED OF MICRO-STRUCTURE BODY

(71) Applicant: THE TRUSTEES OF COLUMBIA UNIVERSITY IN THE CITY OF NEW YORK, New York, NJ (US)

(72) Inventor: Daniel S. Oh, Northvale, NJ (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 15/921,756

(22) Filed: Mar. 15, 2018

(65) Prior Publication Data

US 2019/0054212 A1    Feb. 21, 2019

Related U.S. Application Data

(63) Continuation of application No. 15/082,187, filed on Mar. 28, 2016, now Pat. No. 9,943,626, which is a continuation of application No. PCT/US2014/067375, filed on Nov. 25, 2014.

(60) Provisional application No. 61/909,037, filed on Nov. 26, 2013.

(51) Int. Cl.
| *A61L 27/56* | (2006.01) |
| *A61F 2/28* | (2006.01) |
| *A61L 27/12* | (2006.01) |
| *A61L 27/54* | (2006.01) |
| *A61L 27/26* | (2006.01) |

(52) U.S. Cl.
CPC ............. *A61L 27/56* (2013.01); *A61F 2/28* (2013.01); *A61L 27/12* (2013.01); *A61L 27/26* (2013.01); *A61L 27/54* (2013.01); *A61F 2002/2817* (2013.01); *A61L 2300/41* (2013.01); *A61L 2300/414* (2013.01); *A61L 2430/02* (2013.01)

(58) Field of Classification Search
CPC .......... A61L 27/56; A61L 27/26; A61L 27/54; A61L 27/12; A61F 2/28
See application file for complete search history.

(56) References Cited

U.S. PATENT DOCUMENTS

| 4,789,663 | A | * | 12/1988 | Wallace | .............. | A61L 27/24 |
| | | | | | | 424/423 |
| 5,225,123 | A | | 7/1993 | Torobin et al. | | |
| 5,650,108 | A | | 7/1997 | Nies et al. | | |
| 6,358,532 | B2 | | 3/2002 | Starling et al. | | |
| 2002/0006427 | A1 | * | 1/2002 | Umezu | .............. | A61K 9/1611 |
| | | | | | | 424/423 |
| 2004/0034434 | A1 | | 2/2004 | Evans et al. | | |

(Continued)

OTHER PUBLICATIONS

International Search Report and Written Opinion of the International Searching Authority, United States Patent Office, PCT/US14/67375, dated Apr. 2, 2015.

(Continued)

*Primary Examiner* — Carlos A Azpuru
(74) *Attorney, Agent, or Firm* — Reed Smith LLP; Lisa A. Chiarini

(57) ABSTRACT

A granule form e d from a tubular body having an outer surface and an inner surface separated by a matrix, and at least one core defining an opening extending through the tubular body. The outer surface of the matrix is adapted to permit fluid flow into and out of the matrix.

7 Claims, 9 Drawing Sheets

(56) References Cited

U.S. PATENT DOCUMENTS

2006/0292198 A1    12/2006   Dalal et al.
2008/0281355 A1    11/2008   Mayer et al.
2011/0313538 A1*   12/2011   Oh .......................... A61L 27/56
                                                     623/23.61

OTHER PUBLICATIONS

International Preliminary Report on Patentability, PCT/US14/67375, United States Patent Office, dated May 31, 2016.

* cited by examiner

CORE-CENTERED HYDROXYAPATITE GRANULE COMPOSED OF MICRO-STRUCTURE BODY

CROSS-REFERENCE TO RELATED APPLICATIONS

This application is a continuation of application Ser. No. 15/082,187, filed Mar. 28, 2016, now allowed, which is a continuation of U.S. co-assigned, International Application No. PCT/US2014/067375, filed Nov. 25, 2014, which claims benefit of and priority to U.S. Provisional Application No. 61/909,037 filed Nov. 26, 2013, the contents of which are hereby incorporated by reference in their entirety.

FIELD OF THE DISCLOSED SUBJECT MATTER

The disclosed subject matter is a granule that facilitates cell migration and proliferation and differentiation. The granule has a generally tubular body having an outer surface and at least one inner surface defining one or more cores. A matrix is disposed between the outer surface of the granule and at least one inner surface. Pluralities of granules constitute bone regeneration filler. The granules may be used for orthopedic or dental and craniomaxillofacial applications.

BACKGROUND

Conventional granules used for bone regenerative filler have solid spherical bodies. One drawback of the solid spherical bodies is low population of cell attachment and proliferation as well as a higher fraction of surgical site was occupied by material than core-centered granule, less space for cell ultimately bone regeneration. It has been unexpectedly found that granules having a generally tubular structure with at least one core defined in the body facilitates cell migration and/or proliferation rate.

SUMMARY

In accordance with one aspect of the subject matter, a granule that facilitates cell migration and/or proliferation is provided. The granule has a hollow, tubular body. The tubular body is defined by an outer surface and an inner surface separated by a matrix. The matrix extends between the outer and inner surfaces of the tubular body. The matrix composed of porous micro-structure to facilitate the absorption of natural bone repair-promoting factors in extracellular fluids result in enhancing bone regeneration. The tubular body further includes at least one core which defines an opening extending throughout the tubular body. The core and porous micro-structure permits fluid flow into and out of the tubular body and facilitates cell migration and proliferation within the granule by providing large surface area than solid granule. The micro-structure can be less than 5 micron, or about 10 micron to about 50 micron. The inner core can be less than 150 micron, or about 200 micron to about 500 micron. The granule can be less than 500 micron, or about 1 mm to about 3 mm in length and about 700 micron to about 1500 micron in diameter depending on application.

In one embodiment, the outer surface of the granule is porous. The porous nature of the outer surface permits fluid flow into and out of the granule. The inner surface of the granule defines the outer contours of a core. The defined core extends through the granule body defining the generally tubular structure. The at least one core may be disposed in the center of the granule body or off-center. In some instances, multiple cores are defined in the granule body. For example, in one embodiment, three cores defining three openings through the tubular body exist. The core permits cell migration into the granule.

A matrix interconnects the core and is disposed between the inner and outer surface of the granule body.

In some embodiments, the granule is loaded with beneficial agent. The beneficial agent for example can be a drug including antibacterial or a bio-molecular agent including bone morphogenetic protein or transforming growth factor beta. In one embodiment, the beneficial agent is loaded into the granule by way of biodegradable microspheres. The microspheres may be, for example, disposed in the matrix or attached to the inner or outer surface of the tubular body. In another embodiment, the beneficial agents include an anti-inflammatory agent or a bone growth factor.

In another aspect, a process of fabricating hollow tubular granules, the process comprises: mixing HA powder and water until HA transforms into hollow filaments, subjecting the HA filaments to freezing, and heating the filaments. The mixing step includes stirring the HA until it forms a paste. The freezing step includes subjecting the filaments to liquid nitrogen. The heating step includes a first heating step and a second heating step. The first heating step includes subjecting the filaments to a temperature of about 600° C. for a period of time. The period of time is about one hour. The second heating step includes subjecting the filaments to a temperature of about 1230° C. for a period of time. The period of time is about three hours.

In another aspect, the bone regenerative filler comprising: a plurality of granules, wherein each of the plurality of granules includes a hollow tubular body having an outer surface and an inner surface separated by a matrix, and at least one core defining an opening extending through the tubular body, wherein the outer surface is adapted to permit fluid flow into and out of the matrix. The plurality of granules permits cell migration and proliferation and differentiation. The granules facilitate cell proliferation and differentiation over a period of time. For example, the bone regenerative filler can facilitate migration or proliferation of more than $2 \times 10^5$ cells in less than one week.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIG. 2C shows the availability of drug or beneficial biologic reagent delivery by biodegradable microspheres.

DETAILED DESCRIPTION OF EXEMPLARY EMBODIMENTS

Core-Centered and Porous Ceramic Granule

In one embodiment, macro—(150-500 um) and micro—(5-50 um) structural porous ceramic granules loaded with a beneficial agent are provided. The granule can provide a drug delivery system by using biodegradable polymeric spheres. For example, the granule may be suitable for bone regeneration after damage caused by injury or disease.

Figures 1A, 1B, 1C, 1D:
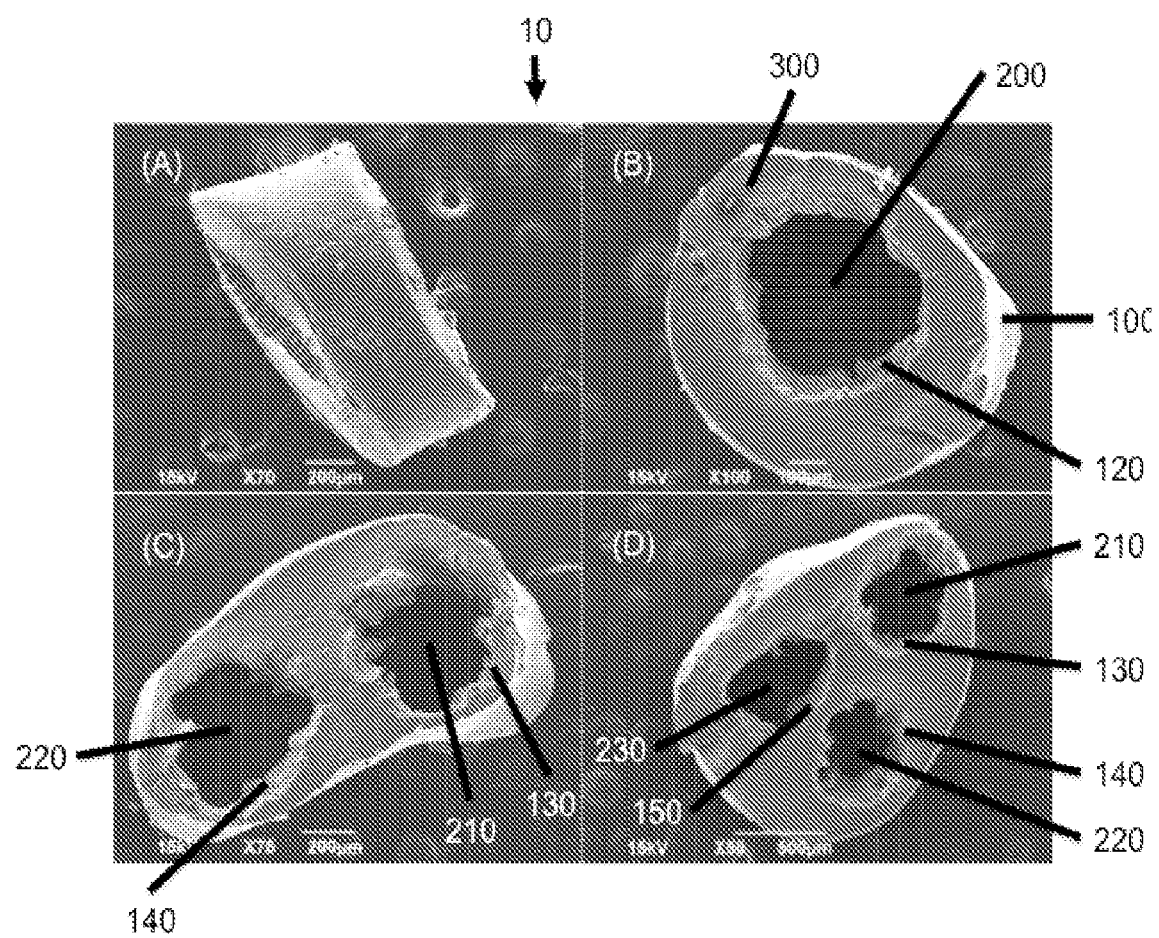
FIG. 1A to 1D are SEM images of granules in accordance with the disclosed subject matter.

As depicted in FIGS. 1A to 1D, a granule 10 having a core-centered structure is depicted. Referring to FIG. 1B, the granule 10 has an outer surface 100, and inner surface 120 and a matrix 300 defined between the inner 120 and outer 100 surfaces. A core 200 is disposed in the granule body and the outer contour of the core 200 is defined by the inner surface 120 of the granule. In one embodiment, as shown in FIGS. 1C and 1D, the granule includes more than one inner surface 130, 140, and 150 defining multiple cores 210, 220, 230.

Figure 2A:
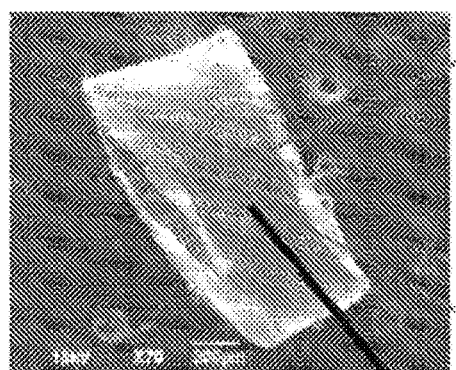
FIG. 2A to 2C shows SEM images of the outer surface and porous micro-structure matrix of the granules shown in FIG. 1.
Figure 2A:
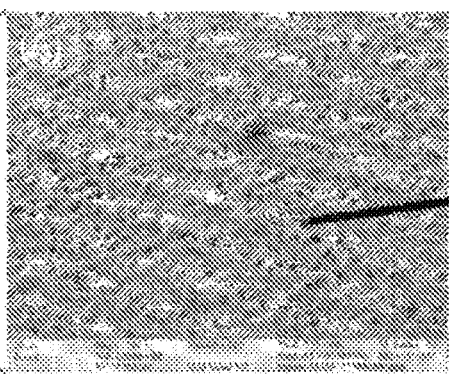
Figure 2B:
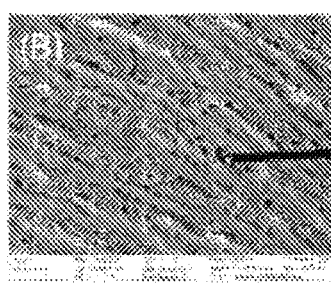
Figure 2C:
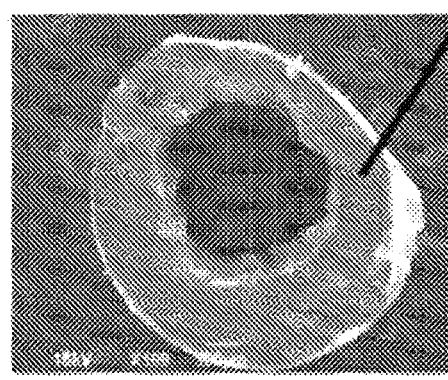
Figure 2C:
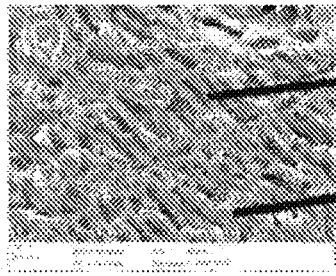
Figure 3:
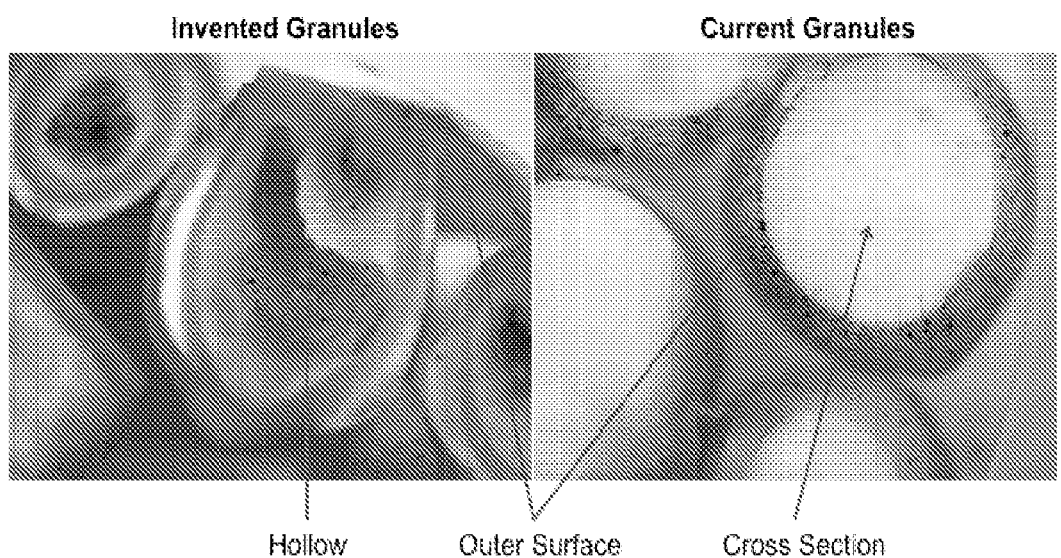
FIG. 3 shows images of the granules of FIG. 1 and granules of the prior art depicting that the granules of FIG. 1 facilitate greater cell migration and exhibit better cell attachment than granules of the prior art.
Figure 4:
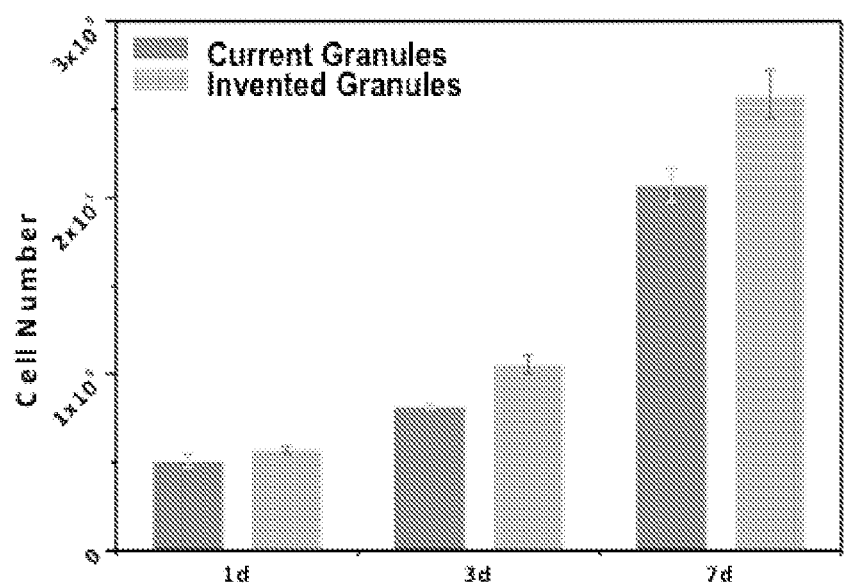
FIG. 4 depicts a comparative MTT assay of the granules in accordance with the disclosed subject matter and the granules of the prior art showing that the granules of the subject application exhibit higher cell proliferation.

The core-centered structure provides a larger surface area for facilitation of cell attachment. The micro-structure 310 in the body shown in FIG. 2B and micro pores 110 on its outer surface shown in FIG. 2A promote fluid flow, such as nutrients and/or natural bone repair-promoting factors but not limited, in and out of the granule. Localized beneficial agents, such as drug or growth factors, can be loaded within the granule. Thus, as shown in FIG. 2C, the granule can provide a delivery system using, for example, biodegradable polymeric microspheres 400 loaded with beneficial agent. Various beneficial agents can be used such as anti-inflammatory agents and bone growth factors but not limited.

Figure 7:
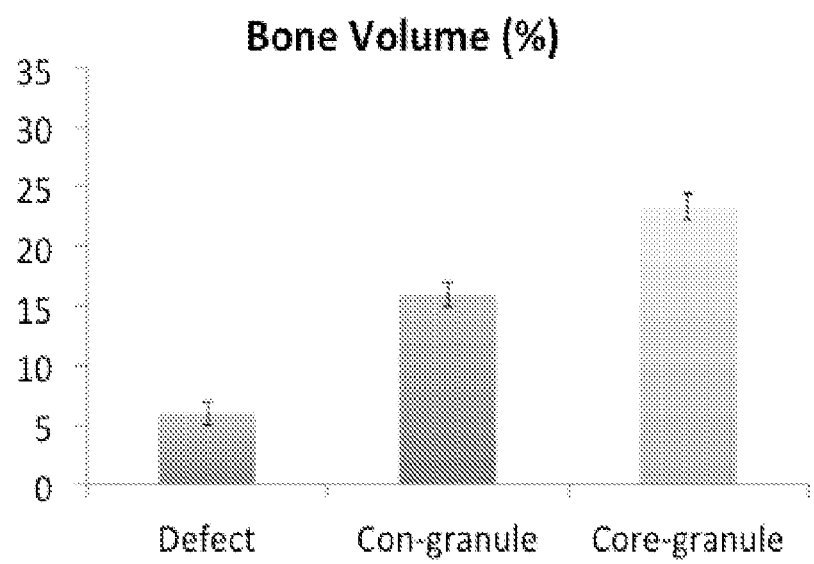
FIG. 7 depicts a comparative bone volume of the granules in accordance with the disclosed subject matter and the granules of the prior art showing that the granules of the subject application exhibit higher new bone formation.
Figure 8:
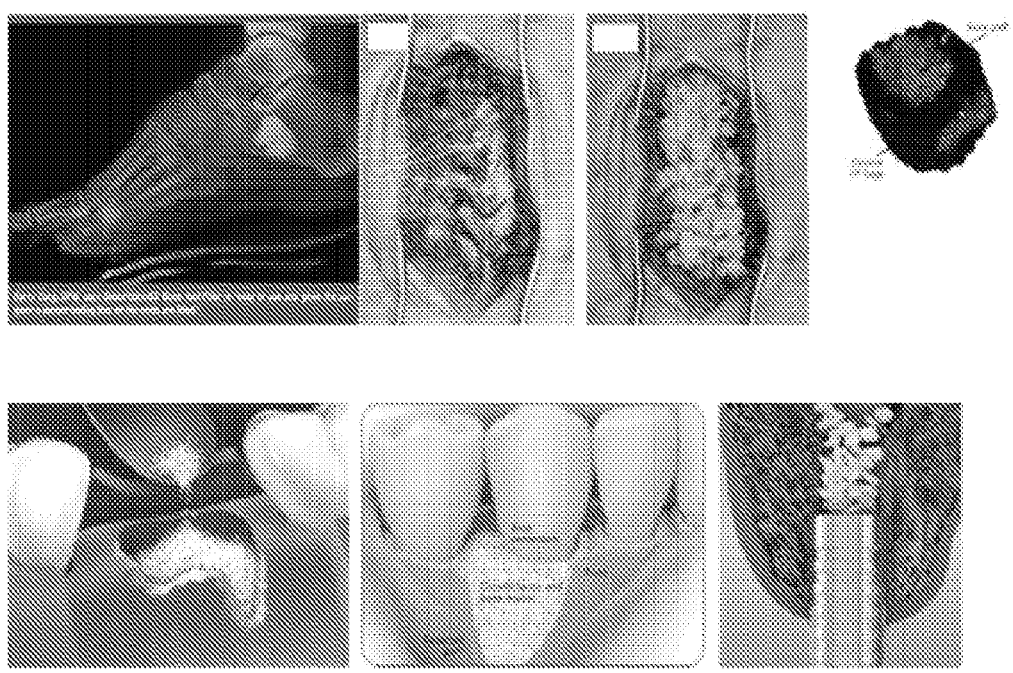
FIG. 8 illustrates various applications of the bone regenerative filler in accordance with the disclosed subject matter.
Figure 9:
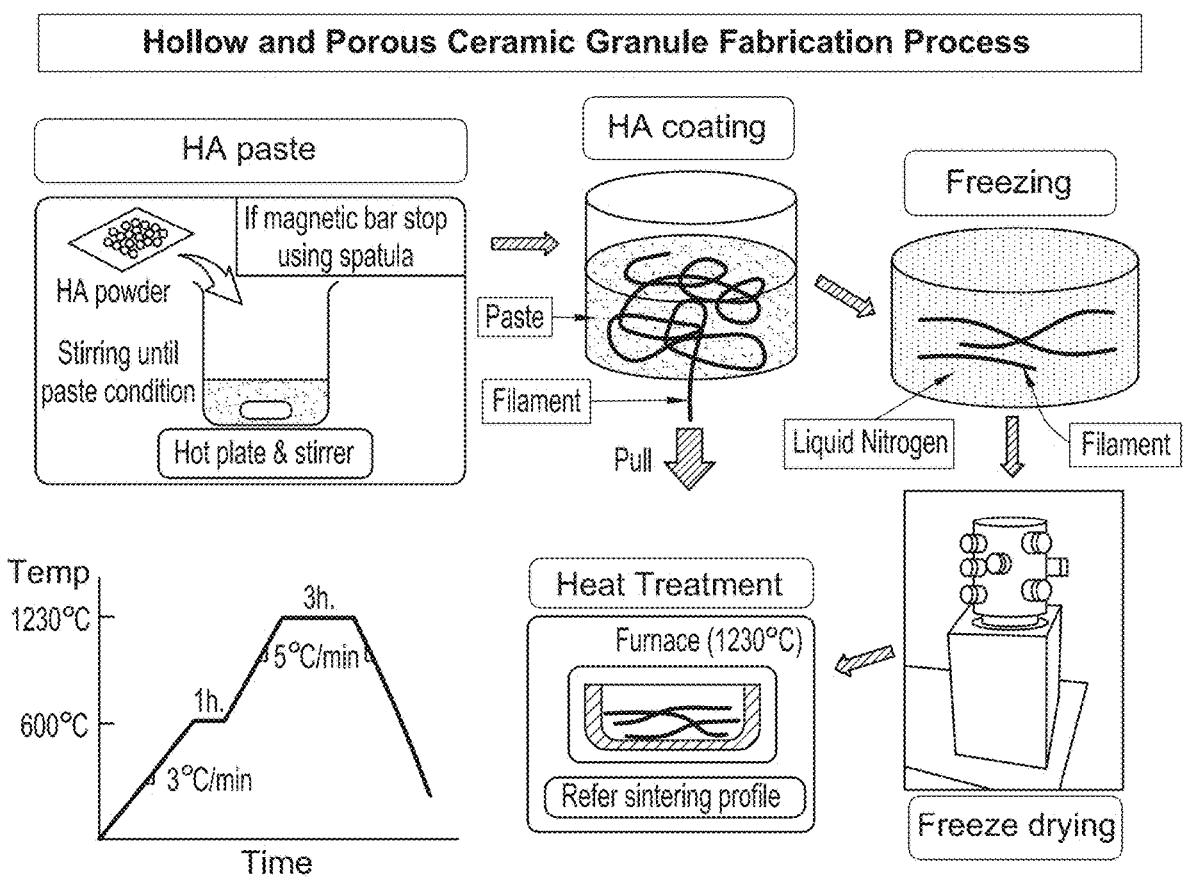
FIG. 9 is a schematic diagram of an exemplary method of making the granule in accordance with the disclosed subject matter.

In another aspect, a method of making the granules is provided. As shown in FIG. 7, one exemplary method for making the granules includes using a water based ceramic slurry coating on fiber filament (thread, twine, yarn, etc.) followed by a freeze-dry method. The ceramic slurry was prepared using hydroxyapatite/solution at a ratio of 0.6-0.7. Binders (3% high molecular weight polyvinyl alcohol, 3% carboxymethylcellulose, and 5% ammonium polyacrylate dispersant) were added to the slurry mixture to improve sintering and the stability of the core-centered granule structure. The filament was coated by prepared HA slurry, then frozen in liquid nitrogen. After complete freeze, it was coated again with HA slurry to freeze in the liquid nitrogen. These steps were repeated until the granule wall attained the desired thickness. The granules were lyophilized using a freeze-dryer overnight. During the lyophilization, the frozen water molecules sublimated and created micro-structures in the body of the granule. Heating followed at 1230° C. for 5 hours by increasing the temperature at a rate of 5° C./min. Then, the furnace was cooled permitting the sintered granules inside to come back down to room temperature at a cooling rate of 5° C./min. During the heat treatment, the filament material dissipated leaving an open core in the granule.

Polymeric Microspheres for Beneficial Agent Delivery

Figures 5A, 5B:
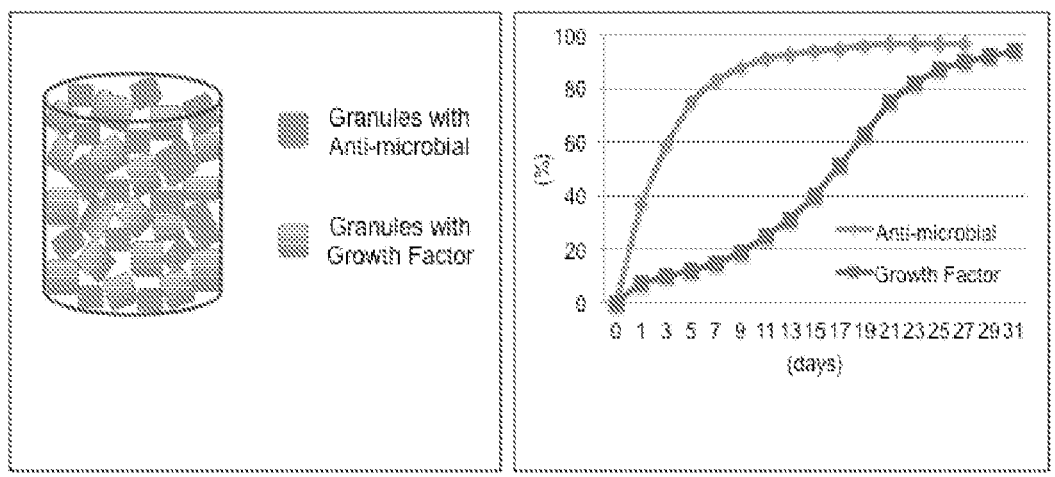
FIG. 5A illustrates a plurality of granules loaded with beneficial agents.
FIG. 5B illustrates an expected release kinetics of the granules of FIG. 5A.
Figure 6:
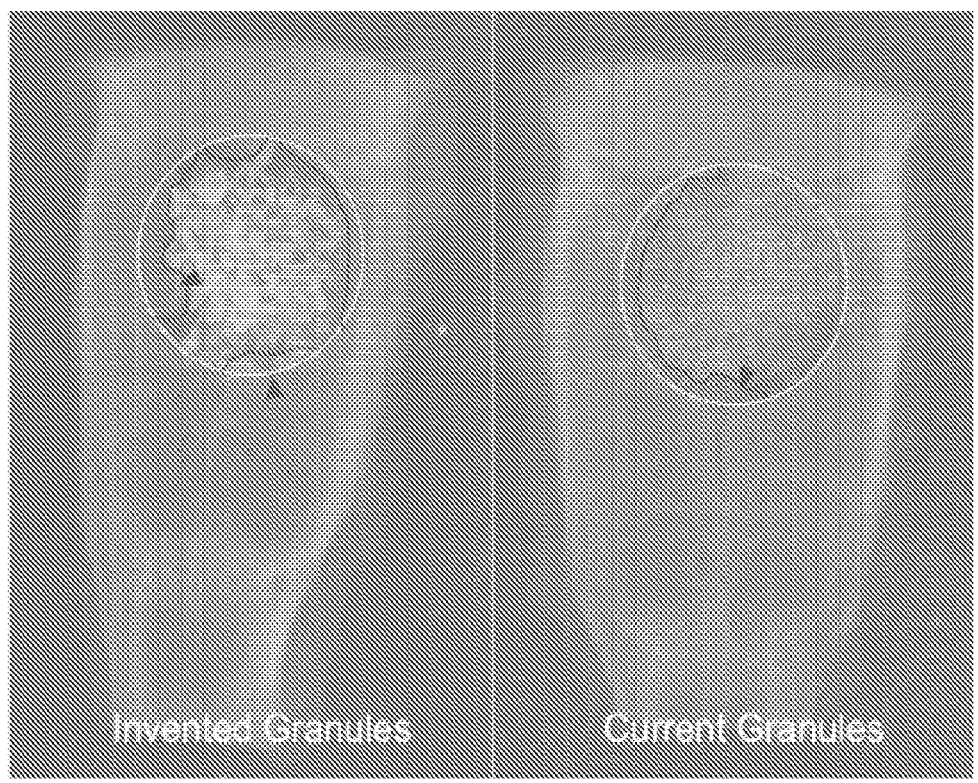
FIG. 6 shows greater new bone formation with invented granules than current granules.

In some embodiments, the granule is loaded with beneficial agent. For example, the beneficial agent can be loaded in microspheres for attachment to the granule body. The non-porous or porous polymeric microspheres for beneficial agent delivery can be fabricated using water/oil (double emersion) or water/oil/water (triple emersion) methods. The polymeric microspheres can be immobilized onto the granule surface and/or inside the micro-structure using electro static techniques. The biodegradable polymeric microspheres can be used as delivery system for antibiotics and/or protein and/or growth factor, etc. After loading the beneficial agent, e.g., the antibiotics and/or protein and/or growth factor, the polymeric microspheres will be attached onto the granules by surface modification by oxygen plasma treatment and/or positive or negative coating method. In this case, after implantation of the granules into a subject, the beneficial agent, e.g., antibiotics, will be released during a first time period e.g., in one week to prevent severe infection of the surgical site. In the second stage protein and/or growth factor or other beneficial agents will be gradually released for up to four weeks to accelerate bone regeneration (FIG. 5B).

For example but without limitation, the granules can be made by hydroxyapatite (HA), tri-calcium phosphate (TCP), HA/TCP composite, any other calcium phosphate family, bio glass, alumina, zirconia, and titanium dioxide, etc. The polymeric microspheres can be made by Polyglycolide (PGA), Poly-L-lactide (PLLA), poly(lactic-co-glycolic acid) (PLGA), Poly-8-caprolactone (PCL), Poly-D, L-lactide (PDLLA), Poly-1,4-dioxane-2-one (PDO), Polytrimethylenecarbonate (PTMC), and Poly-13-hydroxybutyrate (PHB), etc.

The granules can be used directly as a bone substitute without a beneficial agent delivery system. However, the combined system with polymeric microspheres may be useful for bone tumor treatment or periodontal disease treatment.

Cellular Responses for Hollow and Porous HA Granules

Proliferation rate was higher on invented granules than current granules during the observed period of time. Cell attachment was clearly evidenced for both types of granule. However, the invented granule has a hollow structure in the granule body, enhancing cell migration. Based on these findings, the granules disclosed herein can be employed for treatment of bony defects caused either by trauma or massive disease surgeries.

In addition the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

What is claimed is:

1. A process for fabricating hollow tubular granules, the process comprising: mixing hydroxyapatite (HA) powder and water into a slurry, applying the slurry to a filament to form hollow HA filaments, subjecting the HA filaments to freezing, and heating the filaments.

2. The process of claim 1, wherein the freezing step includes subjecting the filaments to liquid nitrogen.

3. The process of claim 1, wherein the heating step includes a first heating step and a second heating step.

4. The process of claim 3, wherein the first heating step includes subjecting the filaments to a temperature of about 600° C. for a period of time.

5. The process of claim 4, wherein the period of time is about one hour.

6. The process of claim 3, wherein the second heating step includes subjecting the filaments to a temperature of about 1230° C. for a period of time.

7. The process of claim 6, wherein the period of time is about three hours.

* * * * *